United States Patent [19]

Natali

[11] Patent Number: 5,052,387

[45] Date of Patent: Oct. 1, 1991

[54] COLD PACK FOR WRAPPING INJURED LIMBS AND METHOD OF MAKING

[76] Inventor: Bernard S. Natali, 6 Laurel Dr., Wallingford, Conn. 06492

[21] Appl. No.: 532,210

[22] Filed: Jun. 1, 1990

[51] Int. Cl.⁵ .............................................. A61F 7/10
[52] U.S. Cl. ...................................... 128/402; 383/63
[58] Field of Search ............... 128/402, 403, 379, 380; 62/530; 383/901, 63, 65

[56] References Cited

U.S. PATENT DOCUMENTS

| | | | |
|---|---|---|---|
| 2,796,903 | 6/1957 | Gazelle | 383/63 |
| 3,226,787 | 1/1966 | Ausnit | 383/65 |
| 4,381,025 | 4/1983 | Schooley | 128/402 |
| 4,530,220 | 7/1985 | Nambu | 128/402 |
| 4,951,666 | 8/1990 | Inman | 128/402 |

Primary Examiner—Edward M. Coven
Assistant Examiner—Mark S. Graham
Attorney, Agent, or Firm—McCormick, Paulding & Huber

[57] ABSTRACT

An ice pack is made from two thermoplastic sheets of polyethylene to provide a rectangular shape that has a small ice compartment defined at one of the rectangle's shorter sides. The opposite short side has a strip of adhesive covered with release paper. In use the ice filled bag end is closed, and the release paper removed so the pack can be conveniently wrapped and secured in place on the injured person.

10 Claims, 2 Drawing Sheets

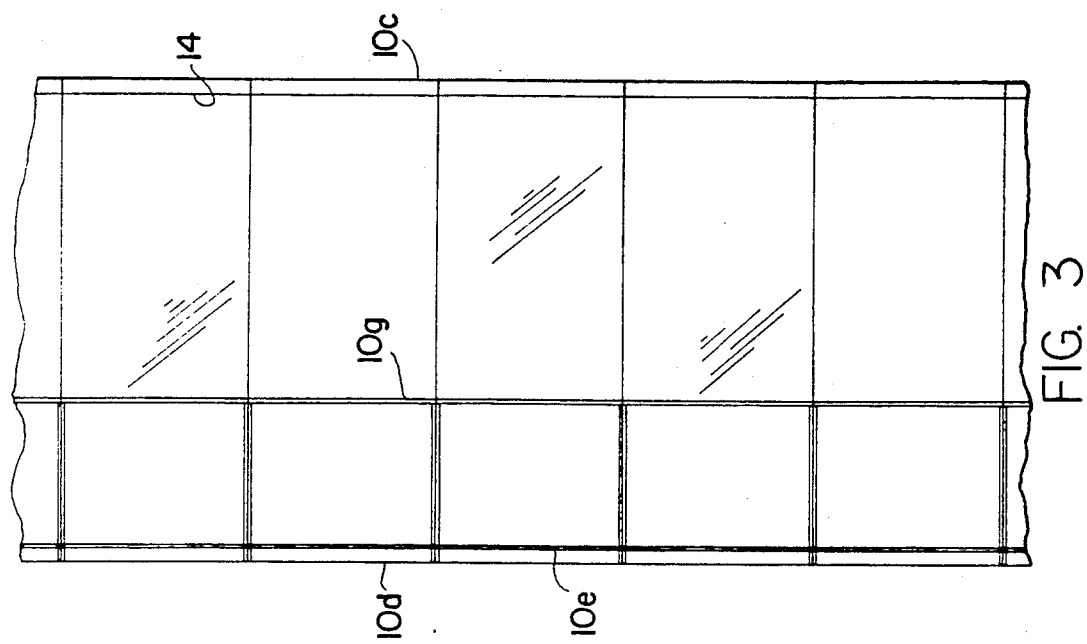
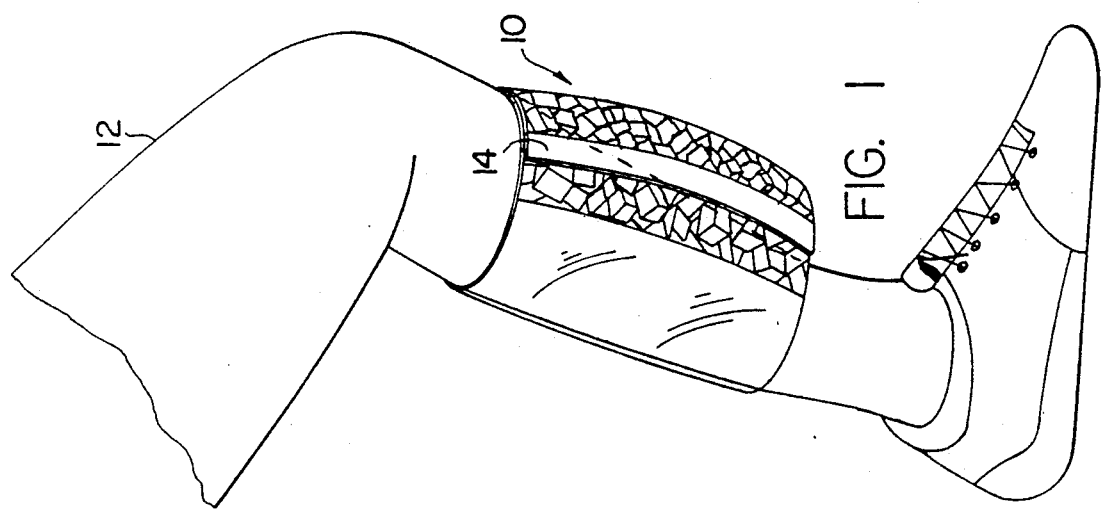

COLD PACK FOR WRAPPING INJURED LIMBS AND METHOD OF MAKING

This invention relates generally to cold packs for wrapping an injured person's limb or other body part and deals more particularly with a relatively inexpensive pack mode from plastic film, which pack not only defines a bladder or reservoir for receiving ice cubes or the like but which also defines a strap portion for securing the bladder or ice pack to the person's limb.

In accordance with the present invention a cold pack is provided comprising a generally rectangular bag formed from thermoplastic film with front and rear panels welded along at least the two long sides of the rectangle and along one short side. The other short side has complimentary ribs integrally formed on the inside surfaces of these panels to permit said other short side to be open or closed. A weld line extends laterally across the front and rear panels connecting these two long sides to define an enclosed void between portions of the panels and to define an inner end of the ice pack compartment itself. This ice pack compartment preferably comprises at least approximately one third the total area of the pack so formed.

SUMMARY OF THE INVENTION

In accordance with the method of the present invention ice packs of the above described variety are fabricated in accordance with a method comprising the following steps:

providing two sheets of thermoplastic film, forming ribs in these sheets on the surfaces that will mate with one another to form a closure adjacent a first marginal edge of the sheets, feeding these sheets in a direction parallel these ribs so that these ribs mate with one another as the sheet are brought into contact with one another, welding the sheets along a second marginal edge opposite the first marginal edge, applying a adhesive layer to one of said sheets adjacent the welded second marginal edge, applying a release paper to this adhesive layer, welding the sheets on a line parallel these first and second marginal edges and in spaced relation there between, welding and cutting these sheets at spaced locations longitudinally of the sheets to form rectangular bags.

DRAWING DESCRIPTION

FIG. 1 is a perspective view illustrating a cold pack construction in accordance with the present invention applied to the leg of an injured athlete.

FIG. 3 is a plan view of a film of plastic sheet in the process of being joined with another such sheet to provide a strip from which the cold packs of FIG. 2 are subsequently formed.

DETAILED DESCRIPTION OF THE PREFERRED EMBODIMENT

Turning now to the drawings in greater detail, a cold pack is illustrated generally at 10 in FIG. 1 for wrapping an injured person's limb, and in the illustration shown this limb comprises a leg 12 and more particularly the lower portion of the leg 12. The cold pack 10 could of course be wrapped around the upper portion of the leg shown or the knee or the ankle or any part of this limb or around any part of any other limb of a person depending upon the anatomical part injured or strained.

Figure 2:
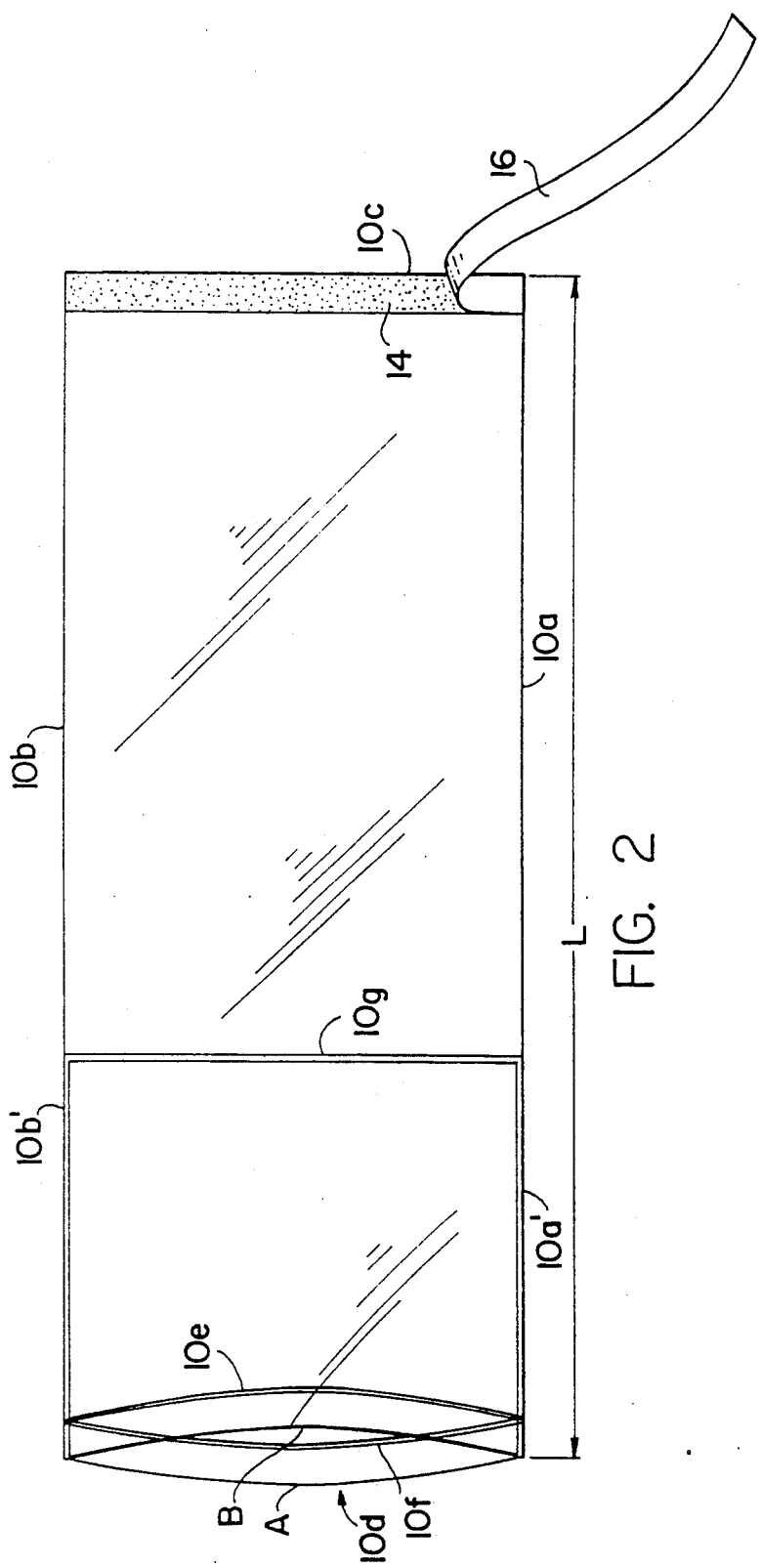
FIG. 2 is a perspective view of the cold pack illustrated in FIG. 1 in position for receiving ice through an open end prior to applying the device to an injured body part as illustrated in FIG. 1.

The ice pack 10 is shown in FIG. 2 as comprising a generally rectangular shape when laid flat and having two long sides $10_a$ and $10_b$ and a short side $10_c$, each of which sides is defined by a weld. The rectangular ice pack is fabricated from two thermoplastic sheets according to a method which will be described hereafter. The fourth side, indicated generally at $10_d$, is provided with integrally formed ribs $10_b$ and $10_f$ that are so configured as to cooperate with one another to permit the open side $10_d$ to be selectively closed.

The two panels A and B from which the cold pack 10 is fabricated are also welded along a line $10_g$ extending laterally across the front and rear panels between the two long sides $10_a$ and $10_b$ and this weld $10_g$ is preferably of a double welded configuration for added strength as are the two parallel segments $10_{a'}$ and $10_{b'}$ of the longer sides $10_a$ and $10_b$ in order to provide a secure compartment or void between the panel portions A and B. As so constructed and arranged ice can be placed in the void defined between the panels A and B and more particularly between the open end $10_d$ and the welded inner end $10_g$ of the compartment or void.

In further accordance with the present invention a strip of adhesive 14 is provided on one of the panels A or B adjacent the short side $10_c$. This adhesive is covered with a release paper 16 that can be conveniently peeled off as suggested in FIG. 2 in order to expose the adhesive layer 14. The ice pack is first filled with ice as described above and then wrapped around the injured person's body part as suggested in FIG. 1 and attached in a secure fashion by means of the adhesive layer 14. This adhesive is preferably of the pressure sensitive type, and may be applied during fabrication of the bag to one panel A or B as described below.

The thermoplastic film used to fabricate a cold pack in accordance with the present invention preferably comprises a polyethylene sheet having a thickness in the range between two and four mils, and is preferably opaque, white being the preferred color for this material. Such a material can be conveniently imprinted with directions as to use of the bag or ice pack, and may of course be imprinted with the logo of the manufacturer.

Figure 4:
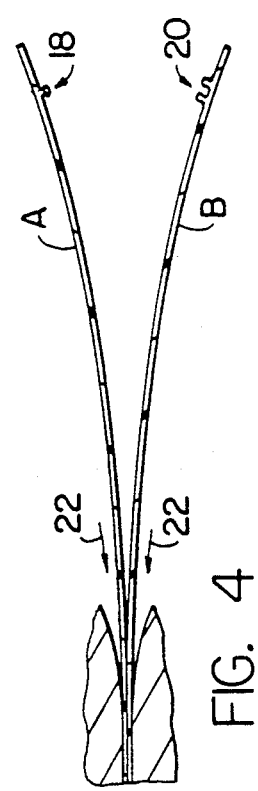
FIG. 4 shows the thermoplastic sheets illustrated in FIG. 3 in a side elevational view and illustrates the preliminary step forming the ribs on the inside or facing surfaces of the sheets to define the complementary ribs to permit releasably closing the ice receiving compartment.

In accordance with the present invention such a bag is preferably fabricated in accordance with a method best described with reference to FIGS. 3 and 4. This method includes the following steps:

Providing two sheets of thermoplastic film as indicated generally at A and B having a width corresponding to the length L of the bag itself. The first step is best shown in FIG. 4 and includes suitable means, indicated generally at 18 and 20, for forming at least one rib in one of these thermoplastic films and a complementary pair of ribs in the other such sheet in order to provide a releasable closure as suggested previously with reference to the ribs $10_e$ and $10_f$ in FIG. 2. If desired two ribs may be formed in one sheet and three in the other to provide a double closure so that melted water from the ice will not be a problem to the person fitted with the cold pack in the manner suggested in FIG. 1. The sheets A and B in FIGS. 3 and 4 are fed in the direction of the arrow 22 at a similar speed and are mated with one another as suggested in FIG. 4. These sheets are welded along marginal edges opposite the first marginal edge as indicated generally at $10_c$, the ribs $10_e$ and $10_f$ being formed in the first marginal edge $10_d$. An adhesive layer 14 is applied to one of these sheets adjacent the welded second marginal edge $10_c$ as shown in FIG. 3.

A release paper 16 (best shown in FIG. 2) is applied to this adhesive layer 14. The welded sheets are further welded along a double weld line $10_g$ parallel said first and second marginal edges $10_c$ and $10_d$ and in spaced relation therebetween. This spacing is preferably such that the area of the panel forming the void for the ice compartment is on the order of one half the area of the remaining ice pack. This geometry provides a sufficient length L for the bag of FIG. 2 so as to permit it to be wrapped around a person's limb as suggested in FIG. 1, and provides a convenient means for locating the ice pack itself in this wrapping process so as to assure that the cold pack is brought into contact with the injured portion of the person's anatomy.

Finally, the rectangular pack of FIG. 2 preferably has short sides that are less than one-half but greater than one-third the length L of the long sides. Again, this geometry assures an efficient size and shape for an ice pack constructed in accordance with the present invention.

I claim:

1. A cold pack for wrapping an injured person's limb or other body part and comprising:

A generally rectangular bag formed from thermoplastic film, said bag including front and rear panels joined along at least the two long sides, said panels being joined also along one short side, another short side opposite said one short side having complementary ribs integrally formed on inside surfaces of these panels to permit said another short side to be opened and closed, a weld line extending laterally across the front and rear panels between said two long sides to define an enclosed void between portions of said panels and to define an inner end of an ice compartment, an outer end of said ice compartment defined by said another short side, and at least one strip of adhesive on one of said panels adjacent said one short side.

2. The cold pack according to claim 1 further including a release paper strip provided over said adhesive strip.

3. The cold pack according to claim 1 wherein said adhesive is of the pressure sensitive type.

4. The cold pack according to claim 1 wherein said thermoplastic film has a thickness in the range of two to four mils.

5. The cold pack according to claim 1 wherein said lateral weld line defines an area for said ice compartment as defined by said panels that is at least approximately one-half the area of said panels between said weld line and said one short side.

6. The cold pack according to claim 1 wherein said rectangular bag has short sides that are less than one-half the length of said long sides.

7. The cold pack according to claim 2 wherein said adhesive is of pressure sensitive type.

8. The cold pack according to claim 7 wherein said thermoplastic film has a thickness in the range of two to four mils.

9. The cold pack according to claim 8 wherein said lateral weld line defines an area for said ice compartment that is at least approximately one-half the size of the area defined between the weld line and said one short side.

10. The cold pack according to claim 9 wherein said rectangular bag short sides are less than one-half the length of said long sides.

* * * * *